(12) United States Patent
Kollet et al.

(10) Patent No.: US 8,029,780 B2
(45) Date of Patent: Oct. 4, 2011

(54) STEM CELLS HAVING INCREASED SENSITIVITY TO A CHEMOATTRACTANT AND METHODS OF GENERATING AND USING SAME

(75) Inventors: Orit Kollet, Ramat Gan (IL); Tsvee Lapidot, Ness Ziona (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 744 days.

(21) Appl. No.: 10/552,331

(22) PCT Filed: Apr. 7, 2004

(86) PCT No.: PCT/IL2004/000315
§ 371 (c)(1),
(2), (4) Date: Jun. 19, 2006

(87) PCT Pub. No.: WO2004/090121
PCT Pub. Date: Oct. 21, 2004

(65) Prior Publication Data
US 2007/0172464 A1 Jul. 26, 2007

(30) Foreign Application Priority Data

Apr. 8, 2003 (IL) .......................... 155303
Dec. 10, 2003 (IL) .......................... 159307

(51) Int. Cl.
C12N 5/07 (2010.01)
C12N 5/071 (2010.01)
(52) U.S. Cl. .................... 424/93.7; 435/325
(58) Field of Classification Search .............. 424/93.7; 435/325
See application file for complete search history.

(56) References Cited

FOREIGN PATENT DOCUMENTS

WO WO-00/06704 2/2000
WO WO-02/50263 6/2002

OTHER PUBLICATIONS

Devine et al. Mesenchymal stem cells are capable of homing to the bone marrow of non-human primates following systemic infusion. Experimental Hematology 29 (2001) 244-255.*
Peled et al. 1999. Dependence of Human Stem Cell Engraftment and Repopulation of NOD/SCID Mice on CXCR4. Science 283: 845-848.*
Kollet et al. 2001. Rapid and efficient homing of human CD34+/CD38-/low/CXCR41 stem and progenitor cells to the bone marrow and spleen of NOD/SCID and NOD/SCID/B2mnull mice. Blood. 97:3283-3291.*
Shi et al. 2007. Regulation of CXCR4 expression in human mesenchymal stem cells by cytokine treatment: role in homing efficiency in NOD/SCID mice. Haematologica 2007; 92:897-904.*
Anfinsen, Science, 181(4096):223-230 (1973).
Armbrust et al., Liver, 22:486-494 (2002).
Banerji et al., Cell, 33:729-740 (1983).
Bongso et al., Hum. Reprod., 4(6):706-713 (1989).
Calame et al., Adv. Immunol., 43:235-275 (1988).
Chan et al., Br. J. Haematol., 112:541-557 (2001).
Comoglio, EXS, 65:131-165 (1993).
Comoglio et al., Exp. Cell Res., 253:88-99 (1999).
Comoglio et al., Genes Cells, 1:347-354 (1996).
Edlund et al., Science, 230:912-916 (1985).
Forbes et al., Clin. Sci. (Lond.), 103:355-369 (2002).
Gao et al., Lancet, 357:932-933 (2001).
Gardner et al., Fertil. Steril., 69(1):84-88 (1998).
Gherardi et al., Nature, 346:228 (1990).
Goddard et al., Transplantation, 72(12):1957-1967 (2001) (http://gateway.ut.ovid.com/gw1/ovidweb.cgi).
Goff et al., Stem Cells, 14:592-602 (1996).
Goldenberg et al., J. Mol. Biol., 165:407-413 (1983).
Grantham, Science, 185:862-864 (1974).
Higashio et al., Biochem. Biophys. Res. Commun., 170:397-404 (1990).
Imai et al., Br. J. Haematol., 106:905-911 (1999).
Korbling et al., N. Engl. J. Med., 346(10):738-746 (2002).
Lapidot et al., Leukemia, 16:1992-2003 (2002).
Lagaaij et al., Lancet, 357:33-37 (2001).
Matsumoto et al., J. Biochem, 119:591-600 (1996).
Mazo et al., J. Leukoc. Biol., 66:25-32 (1999).
McGrath et al., Dev. Biol., 213:442-456 (1999).
Mizuno et al., Biochem. Biophys. Res. Commun., 194(1):178-186 (1993).
Nagasawa et al., Nature, 382:635-638 (1996).
Nakamura et al., Biochem. Biophys. Res. Commun., 122(3):1450-1459 (1984).
Nakamura et al., FEBS Lett., 224(2):311-316 (1987).
Nakamura et al., Nature, 342:440-443 (1989).
Pan et al., Gene, 125:111-114 (1993).
Petit et al., Nat. Immunol., 3(7):687-694 (2002).
Pinkert et al., Genes Dev., 1:268-276 (1987).
Poulsom et al., J. Pathol., 195:229-235 (2001).
Shen et al., Nat. Cell Biol., 2:879-887 (2000).
Shirozu et al., Genomics, 28:495-500 (1995).
Studier et al., Methods Enzymol., 185:60-89 (1990).
Theise et al., Hepatology 31:235-240 (2000).
Theise et al., Hepatology, 32:11-16 (2000).
Thomson et al., Curr. Top. Dev. Biol., 38:133-165 (1998).
Voermans et al., J. Hematother. Stem Cell Res., 10:725-738 (2001).
Weimar et al., Exp. Hematol., 26(9):885-894 (1998).
Whetton et al., Trends Cell Biol., 9:233-238 (1999).
Williams et al., Surg. Forum, 20:293-294 (1969).
Woodbury et al., J. Neurosci. Res., 61:364-370 (2000).
Zarnegar et al., Cancer Res., 49:3314-3320 (1989).

*Primary Examiner* — Taeyoon Kim
(74) *Attorney, Agent, or Firm* — Marshall, Gerstein & Borun LLP

(57) ABSTRACT

The present invention relates to stem cells which exhibit increased sensitivity to a chemoattractant and, more particularly, to methods of generating and using them such as in clinical applications involving stem cell transplantation.

9 Claims, 3 Drawing Sheets

Fig. 1
Fig 1A
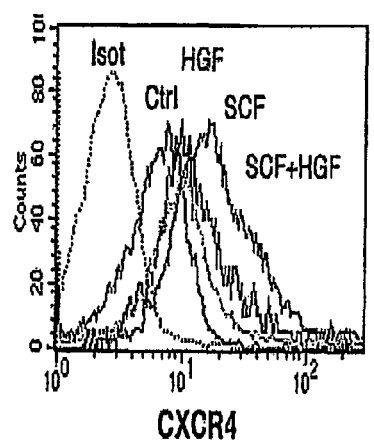
Fig. 1B
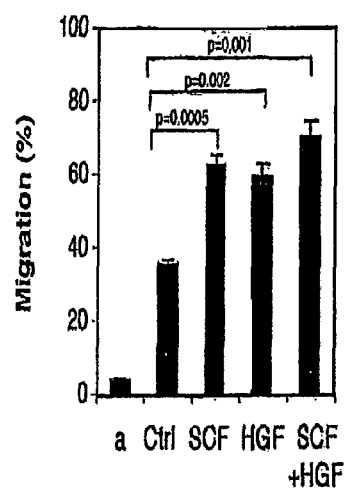

STEM CELLS HAVING INCREASED SENSITIVITY TO A CHEMOATTRACTANT AND METHODS OF GENERATING AND USING SAME

This application is a U.S. National Phase Application pursuant to 35 U.S.C. 371 of International Application No. PCT/IL2004/000315, which was filed Apr. 7, 2004, claiming benefit of priority of Israel Patent Application No. 155303, which was filed Apr. 8, 2003, and Israel Patent Application No. 159307, which was filed Dec. 10, 2003. The entire disclosure of each of the foregoing applications is incorporated herein by reference.

FIELD OF THE INVENTION

The present invention relates to stem cells which exhibit increased sensitivity to a chemoattractant and, more particularly, to methods of generating and using them such as in clinical applications involving stem cell transplantation.

BACKGROUND OF THE INVENTION

Medical treatment of disorders caused by abnormal organ function typically employ pharmaceutical agents designed for either compensating for such abnormal organ function or treating the dysfunctional organ tissue. However, in some cases, pharmaceutical therapy cannot be instated since organ function is oftentimes complex and/or not completely understood.

In such cases, the only viable alternative is surgical replacement of the non-functional organ, which is now widely used for treatment of liver and kidney failure, both acute and chronic, as well as for cancer and certain inborn abnormalities. However, the need for donor organs far exceeds the supply. Organ shortage has resulted in new surgical techniques, such as splitting adult organs for transplant. Despite fairly good results, such techniques still suffer from a lack of donor tissue.

The lack of viable donor tissue has led to the emergence of stem cell replacement therapy, which relies on stem cell plasticity i.e., the ability to give rise to cell types in a new location that are not normally present in the organ in which the stem cells are located.

Stem cells are generally classified according to their origin, essentially adult, embryonic or neonatal origin. Embryonic stem cells deriving from the inner cell mass of the blastocyst are pluripotential, bring capable of giving rise to cells found in all three germ layers. Despite long held belief adult stem cells are not as lineage restricted as previously thought. In particular, haematopoietic and neural stem cells appear to be the most versatile at cutting across lineage boundaries. For example, recent reports suggest that hematopoietic stem cells (HSCs) of human origin have a hepatic potential. Studies of liver or bone marrow transplantation from sex mismatched donors, identified bone marrow-derived hepatocytes in recipients [Alison (2000) Nature 406:257; Theise (2000) Hepatology 32:11-16; Korbling (2002) N Engl J Med 346: 738-746]. Murine and rat HSCs were also found to migrate to irradiated or injured adult livers, and to differentiate into hepatic cells [Petersen (1999) Science 284:1168-1170; Theise (2000) Hepatology 31:235-240; Lagasse (2000) Nat Med 6:1229-1234]. Furthermore, single murine hematopoietic stem cell transplantation has resulted in detection of HSC-derived cells in the liver of irradiated recipients with a low percentage of transplanted cells exhibiting immunohistochemical and morphologic properties of hepatic epithelial cells [Krause (2001) Cell 105:369-377].

The mechanisms that guide circulating hematopoietic stem cells are clinically significant because the success of stem cell transplantation depends on efficient targeting (also referred to as homing) of grafted cells to the recipient target tissue [Mazo and von Adrian (1999) Journal of leukocyte Biology 66,25-32]. It is due to this homing of transplanted cells that bone marrow transplantations do not require invasive surgery, as in the case with the transplantation of any other organ, but rather can be effected by simple intravenous infusion.

Homing of HSCs can be defined as the set of molecular interactions that allows circulating HSCs to recognize, adhere to, and migrate across bone marrow endothelial cells resulting in the accumulation of HSCs in the unique hematopoiesis-promoting microenvironment of the bone marrow. Homing of progenitor cells can be conceived as a multi-step phenomenon [Voermans (2001) J. Hemather. Stem Cell Res. 10:725-738, Lapidot (2002) Leukemia 16:1992-2003]. HSCs arriving to the bone marrow must first interact with the luminal surface of the bone marrow endothelium. This interaction must occur within seconds after the HSCs have entered the bone marrow microvasculature and provide sufficient mechanical strength to permit the adherent cell to withstand the shear force exerted by the flowing blood. Adherent HSCs must then pass through the endothelial layer to enter the hematopoietic compartment. After extravasation, HSCs encounter specialized stromal cells whose juxtaposition supports maintenance of the immature pool by self-renewal process in addition to lineage-specific HSCs differentiation, proliferation and maturation, a process that involves stroma-derived cytokines and other growth signals.

Only a limited number of factors involved in stem cells homing are known to date; these include, the ligand for c-kit, stem cell factor, which has been shown to play a central role in adherence of HSCs to the stroma [Peled (1999) Science 283:845-848]; and integrin interactions (e.g., β1-Intergrins), which were shown to be crucial to the migration of HSCs to the foetal liver [Zanjani (1999) Blood 94:2515-2522].

One important molecular interaction which is considered central to HSC homing is that of chemokine stromal derived factor (SDF-1) and its cognate receptor, CXCR4.

SDF-1 is the only known powerful chemoattractant of hematopoietic stem cells of both human [Aiuti (1997) J. Exp. Med. 185:111-120] and murine origin [Wright (2002) J. Exp. Med. 195:1145-1154] known to date. SDF-1 is widely expressed in many tissues during development [McGrath (1999) Dev. Biol. 213:442-456] and adulthood [Nagasawa (1994) Proc Natl Acad Sci USA 91:2305-2309; Imai (1999) Br J Haematol 106:905-911; Pablos (1999) Am J Pathol 155: 1577-1586], such as for example the liver [Shirozu (1995) Genomics 28:495-500; Nagasawa (1996) Nature 382:635-638; Goddard (2001) Transplantation 72:1957-1967]. Previously, the present inventors were able to show that bone marrow homing and repopulation by sorted human $CD34^+$/$CD38^{-/low}$ stem cells transplanted into the tail vein of irradiated immune deficient NOD/SCID and NOD/SCID/B2m null mice, are dependent on SDF-1/CXCR4 interactions [Peled (1999) Science 283:845-848; Kollet (2001) Blood 97:3283-3291]. More recently, the present inventors also established a role for these interactions in G-CSF-induced mobilization of murine and human stem cells [Petit (2002) Nat Immunol 3:687-694].

In view of the ever-expanding use of stem cell therapy, it is highly desirable to further elucidate the mechanism behind stem cell homing and target repopulation in order to improve the efficiency and success rate of cell replacement therapy.

Hepatocyte growth factor (HGF), initially identified as a potent mitogen for mature hepatocytes, is a kringle-containing polypeptide growth factor sharing structural homology with plasminogen [Nakamure (1984) Biohcem. Biophys. Res. Commun. 122:1450; Nakamura (1987) FEBS Lett. 224: 311; Gohda (1988) J. Clin. Invest. 81:414; Zanegar Cancer Res. 49:3314; Nakamura (1989) Nature 342:440].

HGF is a mesenchyme-derived pleiotropic factor which regulates cell growth, cell motility and morphogenesis in various types of cells [Matsumoto (1993) Goldberg I D, Rosen E M (eds): Hepatocyte Growth Factor-Scatter Factor (HG-SF) and C-met Receptor, Basel, Switzerland, Birkhauser Verlag, 1993, 225; Gherardi (1990) Nature 346: 228; Weidner (1990) J. Cell Biol. 111:2097; Higasho (1990) Biochem. Biophys. Res. Commun. 170:397; Rubin (1991) Proc. Natl. Acad. Sci. USA 88:415]. C-met proto-oncogene is the natural and only receptor for HGF known to date. HGF is considered a humoral mediator of epithelial-mesenchymal interactions responsible for organogenesis of various tissues and organs, regeneration of organs and growth, invasion and metastasis of tumor cells [Matsumoto (1996) J. Biochem. 119:591]. In the hematopoietic system, HGF augments the growth of hematopoietic progenitor cells [Kmiecik (1992) Blood 80:2454; Nishino (1995) Blood 85:3093; Mizuno (1993) Biochem Biophys Res. Commun. 194:178 Galimi (1994) J. Cell Biol. 127:1743). Interestingly, an acute liver injury has been reported to trigger expression of HGF as determined by in-situ hybridization of HGF after stimulation of rat liver with carbon tetrachloride [CCl4, Armbrust (2002) Liver 22:486-494].

Information pertaining to the interaction of HGF with hematopoietic cells is incomplete, although a possible role in hematopoiesis has been suggested. HGF was found to be constitutively produced by human bone marrow stromal cells [Takai (1997) Blood 89:1560-1565]. Recently, HGF was found to be synergistic with GM-CSF and IL-3 in proliferation of murine myeloid progenitor cell line and murine hemopoietic progenitor cells (HPCs) enriched from bone marrow (BM) or fetal liver [Kmiecik (1992) Blood 80:2454-2457; Mizuno (1993) Supra; Nishino (1995) Blood 85:3093-3100]. In addition, a synergistic proliferative effect of HGF with other growth factors on human HPCs has been observed and expression of C-met on CD34+ HPC was detected as well [Galami (1994) J. Cell Biol. 127:1743-1754; Goff (1996) Stem Cells 14:592-602; Weimer (1998) Exp. Hematol. 26:885-894].

While reducing the present invention to practice the present inventors have uncovered that HGF can upregulate CXCR4 expression and promote SDF-1/CXCR4 dependent stem cell motility and migration to the target tissue. These findings provide a novel approach for sensitizing stem cell recruitment to a target tissue and as such can be used in various cell and tissue replacement protocols.

SUMMARY OF THE INVENTION

According to one aspect of the present invention there is provided a method of increasing sensitivity of stem cells to a chemoattractant, the method comprises exposing the stem cells to HGF or an active portion thereof, which is capable of increasing a level of at least one chemoattractant receptor of the stem cells to thereby increase the sensitivity of the stem cells to the chemoattractant.

According to another aspect of the present invention there is provided a method of treating a disorder requiring cell or tissue replacement, the method comprises providing to a subject in need thereof a therapeutically effective amount of stem cells pretreated with HGF or an active portion thereof, which is capable of increasing a level of at least one chemoattractant receptor of the stem cells, thereby treating the disorder requiring cell or tissue replacement in the subject.

According to yet another aspect of the present invention there is provided a method of treating a disorder requiring cell or tissue replacement, the method comprises providing to a subject in need thereof a therapeutic effective amount of HGF or an active portion thereof, which is capable of increasing a level of at least one chemoattractant receptor of stem cells, thereby treating the disorder requiring cell or tissue replacement.

According to still another aspect of the present invention there is provided a use of HGF or an active portion thereof for the manufacture of a medicament for increasing homing of stem cells to a target tissue.

According to an additional aspect of the present invention there is provided a method of generating stem cells suitable for transplantation, the method comprises: (a) collecting stem cells; (b) exposing the stem cells to HGF or an active portion thereof; and (c) isolating stem cells having CXCR4 levels above a predetermined threshold, to thereby generate stem cells suitable for transplantation.

According to further features in preferred embodiments of the invention described below, collecting the stem cells is effected by: (i) a stem cell mobilization procedure; and/or (ii) a surgical procedure.

According to still further features in the described preferred embodiments the isolating stem cells having CXCR4 levels above the predetermined threshold is effected by FACS.

According to still further features in the described preferred embodiments the method further comprises determining homing capabilities of the stem cells having CXCR4 levels above the predetermined threshold following step (c).

According to yet an additional aspect of the present invention there is provided a nucleic acid construct comprising a first polynucleotide sequence encoding HGF or an active portion thereof and an inducible cis-acting regulatory element for directing expression of the polynucleotide in cells.

According to still further features in the described preferred embodiments the inducible cis-acting regulatory element is a shear stress activation element.

According to still further features in the described preferred embodiments the nucleic acid construct further comprises a second polynucleotide sequence being translationally fused to the first polynucleotide sequence, the second polynucleotide sequence encoding a signal peptide capable of directing secretion of the HGF or the active portion thereof out of the cells.

According to still an additional aspect of the present invention there is provided a eukaryotic cell comprising the nucleic acid construct.

According to a further aspect of the present invention there is provided a cell-line comprising stem cells transformed to express an exogenous polynucleotide encoding HGF or an active portion thereof.

According to yet a further aspect of the present invention there is provided a cell culture comprising: (i) stem cells; and (ii) feeder cells expressing HGF or an active portion thereof each being capable of increasing a level of at least one chemoattractant receptor of the stem cells.

According to still a further aspect of the present invention there is provided a method of increasing sensitivity of stem cells to a chemoattractant, the method comprises, upregulating an expression or activity of endogenous HGF or an active portion thereof of the stem cells to thereby increase the sensitivity of the stem cells to the chemoattractant.

According to still a further aspect of the present invention there is provided a method of increasing stem cell motility, the method comprises exposing the stem cells to HGF or an active portion thereof which is capable of increasing motility of the stem cells.

According to still an additional aspect of the present invention the at least one chemoattractant receptor is CXCR4.

According to still an additional aspect of the present invention the method further comprises exposing the stem cells to a growth factor and/or a cytokine.

According to still an additional aspect of the present invention the growth factor and/or cytokine are selected from the group consisting of SCF and IL-6.

According to still an additional aspect of the present invention the stem cells are hematopoietic stem cells.

According to still an additional aspect of the present invention the hematopoietic stem cells are $CD34^+$ hematopoietic stem cells.

According to still an additional aspect of the present invention the hematopoietic stem cells are $CD34^+/CD38^{-/low}$ hematopoietic stem cells.

According to still an additional aspect of the present invention the stem cells are mesenchymal stem cells.

According to still an additional aspect of the present invention exposing the stem cells to the HGF or the active portion thereof, is effected by: (i) expressing a polynucleotide encoding the HGF or the active portion thereof in the stem cells; and/or (ii) contacting the stem cells with the HGF or the active portion thereof.

According to still an additional aspect of the present invention the method further comprises exposing the stem cells to HGF-receptor.

According to still an additional aspect of the present invention provides a method of facilitating self repopulation and/or self engraftment of self progenitor cells to an injured organ, comprising administration of HGF or an active portion thereof alone or together with SCF to a subject suffering of organ inflammation and/or injury.

According to still an additional aspect of the present invention provides a pharmaceutical composition comprising HGF or an active portion thereof which is capable of increasing motility of the stem cells and SCF, and more specifically to a pharmaceutical composition for treating a disorder requiring cell or tissue replacement.

The present invention successfully addresses the shortcomings of the presently known configurations by providing stem cells, which exhibit increased sensitivity to a chemoattractant and methods of generating and using the same.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.
plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1a is a graph depicting cytokine induced expression of CXCR4 in CB $CD34^+$ cells as determined using flow cytometry.

FIG. 1b is a histogram depicting SDF-1 mediated directional migration of $CD34^+$ cells in the presence of HGF, SCF or a combination thereof, as determined using a Transwell migration assay. Data represent percentage of migration. The (a) character denotes spontaneous migration in the absence of SDF-1.

DESCRIPTION OF THE PREFERRED EMBODIMENTS

Figure 2:
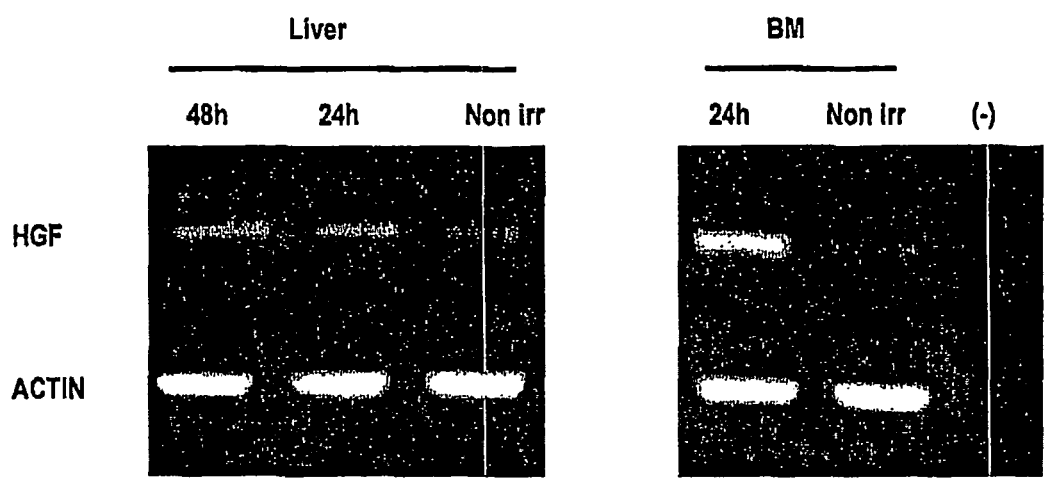
FIG. 2 Shows increased expression of HGF mRNA in the BM and liver of irradiated mice. NOD/SCID mice were sublethally irradiated (375 cGy). Liver and BM samples collected 24 and 48 hours later, together with a sample from a non-irradiated mouse, were homogenized in Tryreagent (MRC). MRNA was extracted using standard protocol. RNA was subjected to RT-PCR.

The present invention relates to stem cells which exhibit increased sensitivity to a chemoattractant and to methods of generating and using the same. Specifically, the present invention allows to treat disorders requiring cell or tissue replacement such as for example to treat chronic or acute liver damage.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The use of cellular therapy is growing rapidly, and is gradually becoming an important therapeutic modality in treatment of various disorders. Hematopoietic stem cell (HSC) (e.g., bone marrow, umbilical cord blood or mobilized peripheral blood) transplantation is one example of a routinely practiced, insurance-reimbursed cellular therapy. However, many other cellular therapies are being developed as well, including immunotherapy for cancer and infectious diseases, chondrocyte therapy for cartilage defects, neuronal cell therapy for neurodegenerative diseases, and stem cell therapy for numerous applications [Forbes (2002) Clinical Science 103:355-369].

One of the problems associated with stem cell therapy is the difficulty of achieving long-term successful engraftment of cells at the target tissue. Currently, patients which were successfully transplanted exhibit very low levels of stem cells and immature progenitors which generate cells with the desired phenotype.

Thus, the success of stem cell transplantation depends on the ability of intravenously infused stem cells to lodge in the target tissue (e.g., bone marrow), a process referred to as homing. It is hypothesized that homing is a multistep process, consisting of adhesion of the stem cells to endothelial cells of the marrow sinusoids, followed by transendothelial migration directed by chemoattractants, and finally anchoring within the extravascular bone marrow spaces where proliferation and differentiation will occur.

Studies have shown that numerous factors are involved in the homing process including, adhesion molecules, cytokines and growth factors. In 1997 studies uncovered that migration of CD34$^+$ cells was goverened by the chemoattractant, SDF-1. Subsequent studies have shown that SDF-1 activates integrins on HSCs and induces trans-endothelial migration of HSCs in vitro. The receptor for SDF-1 is a G-protein coupled receptor, termed CXCR-4. In SDF-1 or CXCR-4 knock-out mice hematopoietic precursors do not shift to the bone marrow during fetal development suggesting that SDF-1/CXCR4 interactions play an important role in stem cell migration [for review see Voermans (2001) J. Hematother. Stem Cell Res. 10:725-738, Lapidot (2002) Leukemia 16:1992-2003].

Despite preliminary understanding of the homing process, information about regulation of migration of stem cells is still incomplete and scattered. It is well appreciated that improving the efficacy of stem cell transplantation may be achieved by modulating the ability of stem cells to home to the target tissue.

While reducing the present invention to practice the present inventors have uncovered that HGF upregulates CXCR4 expression and promotes SDF-1/CXCR4 dependent stem cell motility and migration to a damaged target tissue.

As illustrated hereinunder and in the Examples section which follows, the present inventors illustrate that hepatic injury upregulates HGF, which induces cytoskeletal rearrangements, increases the motility and potentiates the response of immature CD34+ cells to SDF-1 signaling by inducing CXCR4 upregulation and synergizing with stem cell factor (SCF).

Although HGF has been previously shown to be upregulated following liver injury [Armbrust Liver 2002 December; 22(6):486-94], the present inventors are the first to show that this upregulation in HGF activity leads to upregulation in CXCR4 expression to cytoskeletal rearrangements and accelerated homing of cells expressing the same.

The present findings enable the generation of stem cells, which can be efficiently recruited to a target tissue and as such can be used in numerous clinical applications, such as in repair of liver injury and in liver or bone marrow transplantation.

Thus, according to one aspect of the present invention there is provided a method of increasing sensitivity of stem cells to a chemoattractant.

According to another aspect of the present invention there is provided a method comprising the administration of HGF to a subject suffering of organ inflammation and/or injury, to facilitate self repopulation and/or self engraftment to the injured organ, due to increased progenitor stem cell levels in the cell blood circulation.

As used herein, the phrase "stem cells" refers to cells, which are capable of differentiating into other cell types having a particular, specialized function (i.e., "fully differentiated" cells).

The method according to this aspect of the present invention includes exposing the stem cells to HGF or an active portion thereof which is capable of increasing the level of at least one chemoattractant receptor of the stem cells to thereby increase the sensitivity of the stem cells to the chemoattractant.

Alternatively, increasing sensitivity of stem cells to a chemoattractant can also be effected by upregulating expression or activity of endogenous HGF of the stem cells.

As is further described herein under, exposing the stem cells to HGF or an active portion thereof can be effected by either contacting the cells with the protein or an active portion thereof, or by expressing the protein or an active portion thereof within these cells or expressing HGF or an active portion thereof in non-stem cells cultured therewith (e.g., fibroblasts used as a feeder layer).

As is clearly demonstrated in the Examples section which follows, exposure of stem cells to HGF substantially increased their motility and their ability to migrate to a chemoattractant thereof i.e., SDF-1.

The invention relates to HGF and to its salts, functional derivatives, precursors and active fractions as well as its active mutants, i.e. other proteins or polypeptides wherein one or more amino acids of the structure are eliminated or substituted by other amino acids or one or more amino acids were added to that sequence in order to obtain polypeptides or proteins having the same activity of the HGF and comprises also the corresponding "fusion proteins" i.e. polypeptides comprising the HGF or a mutation thereof fused with another protein. The HGF can therefore be fused with another protein such as, for example, an immunoglobulin.

The term "salts" herein refers to both salts of carboxyl groups and to acid addition salts of amino groups of the HGF protein of the invention or muteins thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulphuric acid, and salts with organic acids such as, for example, acetic acid or oxalic acid. Of course, any such salts must have substantially similar activity to the HGF protein of the invention or its muteins.

The definition "functional derivatives" as herein used refers to derivatives which can be prepared from the functional groups present on the lateral chains of the amino acid moieties or on the terminal N- or C-groups according to known methods and are comprised in the invention when they are pharmaceutically acceptable i.e. when they do not destroy the protein activity or do not impart toxicity to the pharmaceutical compositions containing them. Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups.

"Fragment" of the protein the present invention refers to any fragment or precursor of the polypeptidic chain of the compound itself, alone or in combination with related molecules or residues bound to it, for example residues of sugars or phosphates, or aggregates of the polypeptide molecule when such fragments or precursors show the same activity of the HGF as medicament.

The term "circularly permuted" as used herein refers to a linear molecule in which the termini have been joined together, either directly or through a linker, to produce a circular molecule, and then the circular molecule is opened at another location to produce a new linear molecule with termini different from the termini in the original molecule. Circular permutations include those molecules whose structure is equivalent to a molecule that has been circularized and then opened. Thus, a circularly permuted molecule may be synthesized de novo as a linear molecule and never go through a circularization and opening step. The particular circular permutation of a molecule is designated by brackets containing the amino acid residues between which the peptide bond is eliminated. Circularly permuted molecules, which may include DNA, RNA and protein, are single-chain molecules which have their normal termini fused, often with a linker, and contain new termini at another position. See Goldenberg, et al. J. Mol. Biol., 165: 407-413 (1983) and Pan et al. Gene 125: 111-114 (1993), both incorporated by reference herein. Circular permutation is functionally equivalent to taking a straight-chain molecule, fusing the ends to form a circular molecule, and then cutting the circular molecule at a different location to form a new straight chain molecule with different termini. Circular permutation thus has the effect of essentially preserving the sequence and identity of the amino acids of a protein while generating new termini at different locations.

The terms "polypeptide and protein" in the present specification are interchangeable.

The present invention also concerns muteins of the above HGF protein of the invention, which muteins retain essentially the same biological activity of the HGF protein having essentially only the naturally occurring sequences of the HGF. Such "muteins" may be ones in which up to about 20 and 10 amino acid residues may be deleted, added or substituted by others in the HGF protein respectively, such that modifications of this kind do not substantially change the biological activity of the protein mutein with respect to the protein itself.

These muteins are prepared by known synthesis and/or by site-directed mutagenesis techniques, or any other known technique suitable thereof.

Any such mutein preferably has a sequence of amino acids sufficiently duplicative of that of the basic the HGF such as to have substantially similar activity thereto. Thus, it can be determined whether any given mutein has substantially the same activity as the basic protein of the invention by means of routine experimentation comprising subjecting such a mutein to the biological activity tests set forth in Examples below.

Muteins of the HGF protein which can be used in accordance with the present invention, or nucleic acid coding thereof, include a finite set of substantially the HGF corresponding sequences as substitution peptides or polynucleotides which can be routinely obtained by one of ordinary skill in the art, without undue experimentation, based on the teachings and guidance presented herein. For a detailed description of protein chemistry and structure, see Schulz, G. E. et al., Principles of Protein Structure, Springer-Verlag, New York, 1978; and Creighton, T. E., Proteins: Structure and Molecular Properties, W.H. Freeman & Co., San Francisco, 1983, which are hereby incorporated by reference. For a presentation of nucleotide sequence substitutions, such as codon preferences, see. See Ausubel et al., Current Protocols in Molecular Biology, Greene Publications and Wiley Interscience, New York, N.Y., 1987-1995; Sambrook et al., Molecular Cloning: A Laboratory Manual, Cold Spring Harbor Laboratory, Cold Spring Harbor, N.Y., 1989.

Preferred changes for muteins in accordance with the present invention are what are known as "conservative" substitutions. Conservative amino acid substitutions of those in the protein having essentially the naturally-occurring HGF sequences, may include synonymous amino acids within a group, which have sufficiently similar physicochemical properties that substitution between members of the group will preserve the biological function of the molecule, see Grantham, Science, Vol. 185, pp. 862-864 (1974). It is clear that insertions and deletions of amino acids may also be made in the above-defined sequence without altering its function, particularly if the insertions or deletions only involve a few amino acids, e.g., under 50, and preferably under 20 HGF and do not remove or displace amino acids which are critical to a functional conformation, e.g., cysteine residues, Anfinsen, "Principles That Govern The Folding of Protein Chains", Science, Vol. 181, pp. 223-230 (1973). Muteins produced by such deletions and/or insertions come within the purview of the present invention.

Preferably, the synonymous amino acid groups are those defined in Table A. More preferably, the synonymous amino acid groups are those defined in Table B; and most preferably the synonymous amino acid groups are those defined in Table C.

TABLE A

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser. Ala, Gly, His, Gln, Thr |
| Ala | Gly, Thr, Pro, Ala |
| Val | Met, Tyr, Phe, Ile, Leu, Val |
| Gly | Ala, Thr, Pro, Ser. Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Set, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE B

More Preferred Groups of Synonymous Amino Acids

| Amino Acid | Synonymous Group |
|---|---|
| Sers | Sers |
| Arc | His, Lys, Arg |
| Leu | Ile, Phe, Met, Leu |
| Pro | Ala, Pro |
| Thr | Thr |
| Ala | Pro, Ala |
| Val | Met, Ile, Val |
| Gly | Gly |
| Ilea | Ile, Met, Phe, Val, Leu |
| Phe | Met, Tyr, Ile, Leu, Phe |
| Try | Phi, Try |
| Cys | Ser, Cys |

TABLE B-continued
More Preferred Groups of Synonymous Amino Acids

| Amino Acid | Synonymous Group |
|---|---|
| His | Arg, Gln, His |
| Gln | Glu, His, Gln |
| Asn | Asp, Asn |
| Lys | Arg, Lys |
| Asp | Asn, Asp |
| Glu | FLN, Glu |
| Met | Phe, Ile, Val, Leu, Met |
| Trp | Trp |

TABLE C
Most Preferred Groups of Synonymous Amino Acids

| Amino Acid | Synonymous Group |
|---|---|
| Sers | Sers |
| Arc | Arc |
| Leu | Ile, Met, Leu |
| Pro | Pro |
| Thr | Thar |
| Alan | Alan |
| Val | Val |
| Gly | Gly |
| Ilea | Ile, Met, Leu |
| Phi | Phi |
| Try | Tyr |
| Cys | Ser, Cys |
| His | His |
| Gln | Gln |
| Asn | Asn |
| Lys | Lys |
| Asp | Asp |
| Glu | Glu |
| Met | Ile, Leu, Met |
| Trp | Trp |

Examples of production of amino acid substitutions in proteins which can be used for obtaining muteins of the protein for use in the present invention include any known method steps, such as presented in U.S. RE Pat. No. 33,653, U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Straw et al).

In another preferred embodiment of the present invention, any mutein of the HGF protein for use in the present invention has an amino acid sequence essentially corresponding to that of the above noted HGF protein of the invention. The term "essentially corresponding to" is intended to comprehend muteins with minor changes to the sequence of the basic protein which do not affect the basic characteristics thereof, particularly insofar as its ability to the HGF is concerned. The type of changes which are generally considered to fall within the "essentially corresponding to" language are those which would result from conventional mutagenesis techniques of the DNA encoding the HGF protein of the invention, resulting in a few minor modifications, and screening for the desired activity for example increasing the sensitivity of stem cells to a chemoattractant.

The present invention also encompasses HGF variants. A preferred HGF variant are the ones having at least 80% amino acid identity, a more preferred the HGF variant is one having at least 90% identity and a most preferred variant is one having at least 95% identity to HGF amino acid sequence.

The term "sequence identity" as used herein means that the amino acid sequences are compared by alignment according to Hanks and Quinn (1991) with a refinement of low homology regions using the Clustal-X program, which is the Windows interface for the ClustalW multiple sequence alignment program (Thompson et al., 1994). The Clustal-X program is available over the Internet at ftp://ftp-igbmc.u-strasbg.fr/pub/clustalx/. Of course, it should be understood that if this link becomes inactive, those of ordinary skill in the art could find versions of this program at other links using standard Internet search techniques without undue experimentation. Unless otherwise specified, the most recent version of any program referred herein, as of the effective filing date of the present application, is the one, which is used in order to practice the present invention.

Another method for determining "sequence identity" is he following. The sequences are aligned using Version 9 of the Genetic Computing Group's GDAP (global alignment program), using the default (BLOSUM62) matrix (values −4 to +11) with a gap open penalty of −12 (for the first null of a gap) and a gap extension penalty of −4 (per each additional consecutive null in the gap). After alignment, percentage identity is calculated by expressing the number of matches as a percentage of the number of amino acids in the claimed sequence.

Muteins in accordance with the present invention include those encoded by a nucleic acid, such as DNA or RNA, which hybridizes to DNA or RNA under stringent conditions and which encodes a the HGF protein in accordance with the present invention, comprising essentially all of the naturally-occurring sequences encoding the HGF and sequences which may differ in its nucleotide sequence from the naturally-derived nucleotide sequence by virtue of the degeneracy of the genetic code, i.e., a somewhat different nucleic acid sequence may still code for the same amino acid sequence, due to this degeneracy.

The term "hybridization" as used herein shall include any process by which a strand of nucleic acid joins with complementary strand through a base pairing (Coombs J, 1994, Dictionary of Biotechnology, stokton Press, New York N.Y.). "Amplification" is defined as the production of additional copies of a nucleic acid sequence and is generally carried out using polymerase chain reaction technologies well known in the art (Dieffenbach and Dveksler, 1995, PCR Primer, a Laboratory Manual, Cold Spring Harbor Press, Plainview N.Y.).

"Stringency" typically occurs in a range from about Tm−5° C. (5° C. below the melting temperature of the probe) to about 20° C. to 25° C. below Tm.

The term "stringent conditions" refers to hybridization and subsequent washing conditions, which those of ordinary skill in the art conventionally refer to as "stringent". See Ausubel et al., Current Protocols in Molecular Biology, Greene Publications and Wiley Interscience, New York, N.Y., 1987-1995; Sambrook et al., Molecular Cloning: A Laboratory Manual, Cold Spring Harbor Laboratory, Cold Spring Harbor, N.Y., 1989.

As used herein, stringency conditions are a function of the temperature used in the hybridization experiment, the molarity of the monovalent cations and the percentage of formamide in the hybridization solution. To determine the degree of stringency involved with any given set of conditions, one first uses the equation of Meinkoth et al. (1984) for determining the stability of hybrids of 100% identity expressed as melting temperature Tm of the DNA-DNA hybrid:

$$Tm = 81.5C + 16.6(\log M) + 0.41(\% \, GC) - 0.61(\% \, \text{form}) - 500/L$$

where M is the molarity of monovalent cations, % GC is the percentage of G and C nucleotides in the DNA, % form is the percentage of formamide in the hybridization solution, and L is the length of the hybrid in base pairs. For each 1 C that the Tm is reduced from that calculated for a 100% identity hybrid, the amount of mismatch permitted is increased by about 1%. Thus, if the Tm used for any given hybridization experiment at the specified salt and formamide concentrations is 10 C below the Tm calculated for a 100% hybrid according to the equation of Meinkoth, hybridization will occur even if there is up to about 10% mismatch.

As used herein, "highly stringent conditions" are those which provide a Tm which is not more than 10 C below the Tm that would exist for a perfect duplex with the target sequence, either as calculated by the above formula or as actually measured. "Moderately stringent conditions" are those, which provide a Tm, which is not more than 20 C below the Tm that would exist for a perfect duplex with the target sequence, either as calculated by the above formula or as actually measured. Without limitation, examples of highly stringent (5-10 C below the calculated or measured Tm of the hybrid) and moderately stringent (15-20 C below the calculated or measured Tm of the hybrid) conditions use a wash solution of 2×SSC (standard saline citrate) and 0.5% SDS (sodium dodecyl sulfate) at the appropriate temperature below the calculated Tm of the hybrid. The ultimate stringency of the conditions is primarily due to the washing conditions, particularly if the hybridization conditions used are those, which allow less stable hybrids to form along with stable hybrids. The wash conditions at higher stringency then remove the less stable hybrids. A common hybridization condition that can be used with the highly stringent to moderately stringent wash conditions described above is hybridization in a solution of 6×SSC (or 6×SSPE (standard saline-phosphate-EDTA), 5×Denhardt's reagent 0.5% SDS, 100 µ g/ml denatured, fragmented salmon sperm DNA at a temperature approximately 20 to 25 C below the Tm. If mixed probes are used, it is preferable to use tetramethyl ammonium chloride (TMAC) instead of SSC (Ausubel, 1987, 1999).

Non-limiting examples of stem cells, which can be used according to this aspect of the present invention, are hematopoietic stem cells (HSCs) and mesenchymal stem cells (MSCs) obtained from bone marrow tissue of an individual at any age or from cord blood of a newborn individual, embryonic stem (ES) cells obtained from the embryonic tissue formed after gestation (e.g., blastocyst), or embryonic germ (EG) cells obtained from the genital tissue of a fetus any time during gestation, preferably before 10 weeks of gestation. Further description of stem cells, which can be used according to this aspect of the present invention is summarized hereinbelow.

HSCs—Hematopoietic stem cells (HSCs) are the formative pluripotential blast cells found inter alia in bone marrow, fetal liver, umbilical cord blood and peripheral blood which are capable of differentiating into any of the specific types of hematopoietic or blood cells, such as erythrocytes, lymphocytes, macrophages and megakaryocytes. Typically, within the bone marrow, HSCs reside in niches that support all the requisite factors and adhesive properties to maintain their ability and produce an appropriate balanced output of mature progeny over the life time of the organism [Whetton (1999) Trends Cell Biol 9:233-238; Weissman (2000) Cell 100:157-168; Jankowska-Wieczorek (2001) Stem Cells 19:99-107; Chan (2001) Br. J. Haematol. 112:541-557].

HSCs according to this aspect of the present invention are preferably CD34$^+$ cells and more preferably CD34$^+$/CD38$^{-/low}$ cells, which are a more primitive stem cell population and are therefore less lineage-restricted and are the major long-term bone marrow repopulating cells.

MSCs—Mesenchymal stem cells are the formative pluripotential blast cells found inter alia in bone marrow, blood, dermis and periosteum that are capable of differentiating into more than one specific type of mesenchymal or connective tissue (i.e. the tissues of the body that support the specialized elements; e.g. adipose, osseous, stroma, cartilaginous, elastic and fibrous connective tissues) depending upon various influences from bioactive factors, such as cytokines.

Approximately, 30% of human marrow aspirate cells adhering to plastic are considered as MSCs. These cells can be expanded in vitro and then induced to differentiate. The fact that adult MSCs can be expanded in vitro and stimulated to form bone, cartilage, tendon, muscle or fat cells render them attractive for tissue engineering and gene therapy strategies. In vivo assays have been developed to assay MSC function. MSCs injected into the circulation can integrate into a number of tissues described hereinabove. Specifically, skeletal and cardiac muscle can be induced by exposure to 5-azacytidine and neuronal differentiation of rat and human MSCs in culture can be induced by exposure to β-mercaptoethanol, DMSO or butylated hydroxyanisole [Tomita (1999) 100: 11247-11256; Woodbury (2000) J. Neurosci. Res. 61:364-370]. Furthermore, MSC-derived cells are seen to integrate deep into brain after peripheral injection as well as after direct injection of human MSCs into rat brain; they migrate along pathways used during migration of neural stem cells developmentally, become distributed widely and start lose markers of HSC specialization [Azizi (1998) Proc. Natl. Acad. Sci. USA 95:3908-3913]. Methods for promoting mesenchymal stem and lineage-specific cell proliferation are disclosed in U.S. Pat. No. 6,248,587.

Epitopes on the surface of the human mesenchymal stem cells (hMSCs) such as SH2, SH3 and SH4 described in U.S. Pat. No. 5,486,359 can be used as reagents to screen and capture mesenchymal stem cell population from a heterogeneous cell population, such as exists, for example, in bone marrow. Precursor mesenchymal stem cells which are positive for CD45 are preferably used according to this aspect of the present invention, since these precursor mesenchymal stem cells can differentiate into the various mesenchymal lineages.

Preferred stem cells according to this aspect of the present invention are human stem cells.

Table 1, below provides examples of adult stem cells, which can be used to obtain the indicated phenotype in a target tissue of interest, according to this aspect of the present invention.

TABLE 1

| Stem cell | Differentiated phenotype | Target tissue | Reference |
|---|---|---|---|
| Bone marrow | Oval cells, Hepatocytes | Liver | Petersen (1999) Science 284: 1168-1170 |

TABLE 1-continued

| Stem cell | Differentiated phenotype | Target tissue | Reference |
|---|---|---|---|
| KTLS cells | Hepatocytes | Liver | Lagasse (2000) Nat. Med. 6: 1229-1234 |
| Bone marrow | Hepatocytes | Liver | Alisan (2000) Nature 406: 257; Thiese (2000) Hepatology 32: 11-16 |
| Pacreatic exocrine cells | Hepatocytes | Liver | Shen (2000) Nat. Cell Biol. 2: 879-887 |
| Pacreas | Hepatocytes | Liver | Wang (2001) Am. J. Pathol. 158: 571-579 |
| Bone marrow | Endothelium | Liver | Gao (2001) Lancet 357: 932-933 |
| Bone marrow | Tubular epithelium, glomeruli | Kidney | Poulsom (2001) J. Pathol. 195: 229-235 |
| Bone marrow | Endothelium | Kidney | Lagaaij (2001) Lancet 357: 33-37 |
| Extra renal | Endothelium | Kidney | Williams (1969) Surg. Forum 20: 293-294 |
| Bone marrow | Myocardium | Heart | Orlic (2001) Nature 410: 701-704 |
| Bone marrow | Cardiomyocytes and Endothelium | Heart | Jackson (2001) J. Clin Invest. 107: 1395-1402 |
| Bone marrow | Type 1 pneumocytes | Lung | Krause (2001) Cell 105: 369-377 |
| Neuronal | Multiple hematopoietic lineages | Marrow | Bjornson (1999) Science 283: 534-537 |
| Bone marrow | Neurons | CNS | Mezey (2000) Science 290: 1779-1782 |
| Bone marrow | Microglia and Astrocyes | CNS | Eglitis (1997) Proc. Natl. Acad. Sci. USA 94: 4080-4085 |

Abbreviations:
SP—Side population cells;
CNS—central nervous system;

As mentioned hereinabove the stem cells according to this aspect of the present invention are exposed to HGF or an active portion thereof.

HGF is a heterodimeric polypeptide including a 62 kDa α-subunit and a 34 kDa β-subunit. The α-subunit contains an N-terminal hairpin domain including 27 amino acids followed by four canonical kringle domains which are 80-amino acid double looped structures stabilized by three internal disulfide bridges [Comoglio (1999) Exp. Cell. Res. 253:88-99; Comoglio (1993) Exs 65:131-65; Comoglio (1996) Genes Cells 1:347-54]. The kringle domains are important for protein-protein interaction. The first kringle domain contains the high affinity binding domain for the HGF-receptor, while the second kringle domain contains a low affinity binding site to membrane associated heparan-sulfate proteoglycans. The low affinity interaction maintains a high concentration of HGF in the vicinity of target cells. The HGF gene encodes a single pro-HGF protein, which is cleaved to form the active heterodimeric molecule with high affinity for the receptor.

As used herein an active portion of HGF, refers to the minimal HGF sequence, which is sufficient to increase sensitivity of the stem cells of the present invention to the chemoattractant As used herein an active portion of HGF, refers also to a mutein, fusion protein, functional derivative, fragment, circularly permutated HGF and/or salt thereof.

To determine the active portion of HGF according to the present invention, stem cells can be contacted with an HGF segment and response of the cells thereto can be monitored molecularly, biochemically or functionally (e.g., motility, homing, migration assays) using methods which are well known to those of skill in the art and are further described hereinbelow.

As described hereinabove exposing the stem cells to HGF or an active portion thereof increases the level of at least one type of chemoattractant receptor of the stem cells.

A number of chemotactic cell receptors are known to participate in transendothelial migration of stem cells. Many of these receptors belong to the family of G protein-coupled seven-transmembrane receptors (7-TMR). Signaling via G proteins, particularly Gi proteins, results in a chemotactic response of the cells towards a gradient of the corresponding ligand [Voermans (2001) J. Hematother. Stem Cell Res. 10:725-738]. Recent studies have provided evidence for expression of several 7-TMR on immature hematopoietic progenitor cells, which potentially mediate chemotactic effects: chemokine receptors (e.g., CXCR4, receptor for stromal cell-derived factor-1), receptors for lipid mediators (e.g., the cysteinyl leukotriene receptor cysLT1 and the peripheral cannabinoid receptor cb2), and receptors for neuroendocrine hormones (e.g., the somatostatin receptor sst2). From these studies it can be concluded that migration of hematopoietic progenitor and stem cells is controlled by a variety of chemotactic factors rather than by a single chemokine (e.g., SDF-1).

According to preferred embodiments of this aspect of the present invention the chemotactic receptor is CXCR4.

It will be appreciated that since HGF exerts its biological activities through binding to an HGF-receptor i.e., c-met, the present invention also contemplates exposing the cells to HGF receptor, i.e. c-met which may be a limiting factor in HGF-signaling.

As mentioned hereinabove, exposing the stem cells to HGF or an active portion thereof can be effected by contacting the stem cells with the protein or by expressing the protein within the stem cells.

Contacting stem cells with HGF or an active portion thereof is preferably effected using harvested cells, although the present invention also contemplates mobilization of stem cells from tissue into circulation and exposure of circulating stem cells to the HGF or an active portion thereof.

Adult stem cells can be obtained using a surgical procedure such as bone marrow aspiration or can be harvested using commercial systems such as those available from Nexell Therapeutics Inc. Irvine, Calif., USA.

Stem cells utilized by the present invention are preferably collected (i.e., harvested) using a stem cell mobilization procedure, which utilizes chemotherapy or cytokine stimulation to release of HSCs into circulation of subjects. Stem cells are preferably retrieved using this procedure since mobilization is known to yield more is HSCs and progenitor cells than bone marrow surgery.

Stem cell mobilization can be induced by a number of molecules. Examples include but are not limited to cytokines such as, granulocyte colony-stimulating factor (G-CSF), granulocyte-macrophage colony-stimulating factor (GM-CSF), interleukin (IL)-7, IL-3, IL-12, stem cell factor (SCF), and flt-3 ligand; chemolines like IL-8, Mip-1α, Groβ, or SDF-1; and the chemotherapeutic agents cyclophosphamide (Cy) and paclitaxel. It will be appreciated that these molecules differ in kinetics and efficacy, however, according to presently known embodiments G-CSF is preferably used alone or in combination such as with cyclophosphamide to mobilize the stem cells. Typically, G-CSF is administered daily at a dose of 5-10 µg/kg for 5-10 days. Methods of mobilizing stem cells are disclosed in U.S. Pat. Nos. 6,447,766 and 6,162,427.

Human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 1-2 weeks. For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; Gardner et al., [Fertil. Steril. 69: 84, 1998].

It will be appreciated that commercially available stem cells can be also be used according to this aspect of the present invention. Human ES cells can be purchased from the NIH human embryonic stem cells registry (<http://escr.nih.gov>). Non-limiting examples of commercially available embryonic stem cell lines are BG01, BG02, BG03, BG04, CY12, CY30, CY92, CY10, TE03, TE32.

Human EG cells can be retrieved from the primordial germ cells obtained from human fetuses of about 8-11 weeks of gestation using laboratory techniques known to anyone skilled in the arts. The genital ridges are dissociated and cut into small chunks, which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparing EG cells see Shamblott et al., [Proc. Natl. Acad. Sci. USA 95: 13726, 1998] and U.S. Pat. No. 6,090,622.

It will be appreciated that enrichment of stem cell population exhibiting pluripotency may be preferably effected. Thus, for example, as outlined hereinabove, CD34$^+$ stem cells can be concentrated using affinity columns or FACS as further described hereinunder.

Culturing of stem cells under proliferative conditions may also be effected in cases where stem cell numbers are too low for use in treatment Culturing of stem cells is described in U.S. Pat. Nos. 6,511,958, 6,436,704, 6,280,718, 6,258,597, 6,184,035, 6,132708 and 5,837,5739.

Once stem cells are obtained, they are contacted with HGF or an active portion thereof.

Soluble HGF, and in particular, active portion thereof can be biochemically synthesized by using, for example, standard solid phase techniques. These methods include exclusive solid phase synthesis, partial solid phase synthesis methods, fragment condensation, classical solution synthesis. Solid phase peptide synthesis procedures are well known in the art and further described by John Morrow Stewart and Janis Dillaha Young, Solid Phase Peptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

It will be appreciated that HGF can also be obtained from commercial suppliers such as, Sigma-Aldrich, Rehovot, Israel; Product No. H1404.

In cases where large amounts of HGF or the active portion thereof are desired, such polypeptides are preferably generated using recombinant techniques.

To recombinantly synthesize such polypeptides, an expression construct (i.e., expression vector), which includes a polynucleotide encoding the HGF or the active portion thereof positioned under the transcriptional control of a regulatory element, such as a promoter, is introduced into host cells.

The "transformed" cells are cultured under suitable conditions, which allow the expression of the fusion protein encoded by the polynucleotide.

Following a predetermined time period, the expressed protein is recovered from the cell or cell culture, and purification is effected.

A variety of prokaryotic or eukaryotic cells can be used as host-expression systems to express the modified polypeptide coding sequence. These include, but are not limited to, microorganisms, such as bacteria transformed with a recombinant bacteriophage DNA, plasmid DNA or cosmid DNA expression vector containing the desired coding sequence; Mammalian expression systems are preferably used to express the HGF or the active portion thereof, since eukaryotic cells enable the generation of post-translational modified proteins. However, bacterial systems are typically used to produce recombinant proteins since they enable a high production volume at low cost. Thus, the host system is selected according to the recombinant protein to be generated and the end use thereof.

In bacterial systems, a number of expression vectors can be advantageously selected depending upon the use intended for the modified polypeptide expressed. For example, when large quantities of conjugates are desired, vectors that direct the expression of high levels of the protein product, possibly as a fusion with a hydrophobic signal sequence, which directs the expressed product into the periplasm of the bacteria or the culture medium where the protein product is readily purified may be desired. Certain fusion protein engineered with a specific cleavage site to aid in recovery of the conjugate may also be desirable. Such vectors adaptable to such manipulation include, but are not limited to, the pET series of *E. coli* expression vectors [Studier et al. (1990) Methods in Enzymol. 185:60-89).

Other expression systems such as insects and mammalian host cell systems, which are well known in the art can also be used by the present invention (see U.S. Pat. No. 6,541,623).

In any case, transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant modified polypeptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

The resultant recombinant proteins of the present invention are preferably secreted into the growth (e.g., fermentation) medium.

Following a predetermined time in culture, recovery of the recombinant protein is effected. The phrase "recovering the recombinant protein" refers to collecting the whole growth medium containing the protein and need not imply additional steps of separation or purification (see Example 2 of the Examples section). Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Proteins of the present invention are preferably retrieved in "substantially pure" form. As used herein, "substantially pure" refers to a purity that allows for the effective use of the protein in the diverse applications, described hereinbelow.

It will be appreciated that recombinant production of HGF or the active portion thereof of the present invention can also be effected in-vitro.

HGF or the active portion thereof can be included in a culture medium utilized for culturing or sustaining the harvested stem cells. Such a culture medium typically includes a buffer solution (i.e., growth medium) suitable for stem cell culturing. The culture medium can also include serum or serum replacement which include growth factors which support growth and survival of the stem cells. The culture medium can also include homing agents such as SDF-1, IL-6, SCF and the like. Additionally the growth medium of the present invention may also include differentiation-inhibiting agents such as leukemia inhibitor factor (LIF).

The stem cells of the present invention can also be contacted with HGF secreting cells. This can be effected by co-culturing the stem cells of the present invention with cells which express HGF or an active portion thereof. For example, fibroblast feeder cells, which are oftentimes-co-cultured with stem cells to support proliferation thereof in a non-differentiated state, can express HGF, thereby performing a dual role i.e., growth support and increase of migration and motility potential of stem cells.

However since the stem cells of the present invention are preferably used for clinical applications, measures are taken to isolate the stem cells from the second HGF-expressing cell population following induction of sufficient level of the at least one chemoattractant receptor of the stem cells. Methods of sorting cell populations are further described hereinbelow.

Alternatively, the stem cells of the present invention can be transformed with an expression construct such as that described above in order to express HGF or the active portion thereof in the stem cells.

In such cases, the expression construct includes a cis-acting regulatory element active in mammalin cells (examples above), preferably under inducible, growth specific or tissue specific conditions.

Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166). The nucleic acid construct of the present invention can further include an enhancer, which can be adjacent or distant to the promoter sequence and can function in up regulating the transcription therefrom.

Preferably, the inducible cis-acting regulatory element is regulatable by changes in the environment of the stem cells during the homing-implantation process.

During their migration, stem cells are subjected to shear forces generated by movement of the cells within circulating blood; once implanted, stem cells are no longer subjected to such shear forces. Since the HGF is preferably active during the homing stage (migration), the use of a cis-acting regulatory element which is active only at the stage of migration is particularly advantageous. One such regulatory element is the shear stress responsive element described by Resnick et al., in PNAS USA 90:4591-4595, 1993.

Genetic modification of mesenchymal stem cells is discussed in U.S. Pat. No. 5,591,625. Genetic modofocation of HSCs is discussed in Zheng 2000 Nat. Biotechnol. 18:176-180 and Lotti 2002 J. Virol. 76(8)3996-4007.

Once exposed to HGF or an active portion thereof, stem cells exhibiting increased expression levels of the chemoattractant receptor and as a result, increased sensitivity to the chemoattractant are preferably identified and isolated. Although such a step enriches for highly chemotactic cells, use of a non-enriched HGF-treated population is also envisaged by the present invention.

Identification and isolation of such cells according to this aspect of the present invention can be effected using a number of cytological, biochemical and molecular methods which are well known in the art.

For example, analysis of receptor level can be effected by flow cytometry. This approach employs instrumentation that scans single cells flowing past excitation sources in a liquid medium. The technology can provide rapid, quantitative, multiparameter analyses on single living (or dead) cells based on the measurement of visible and fluorescent light emission. This basic protocol focuses on: measure fluorescence intensity produced by fluorescent-labled antibodies and ligands that bind specific cell-associated molecules. To isolate cell populations using fluorescence activated cell sorter stem cells of the present invention are contacted with anti CXCR4 commercially available from R&D, 614 McKinley Place NE Minneapolis, Minn.

Other cytological or biochemical methods for quantitatively assessing the level of the chemotactic receptor expression include but are not limited to binding analysis using a labeled (e.g., radioactively labeled) chemokine, western blot analysis, cell-surface biotinylation and immunofluorescent staining.

It will be appreciated that the receptor expression levels can also be determined at the mRNA level. For example, CXCR4 mRNA may be detected in cells by hybridization to a specific probe. Such probes may be cloned DNAs or fragments thereof, RNA, typically made by in-vitro transcription, or oligonucleotide probes, usually generated by solid phase synthesis. Methods for generating and using probes suitable for specific hybridization are well known and used in the art. Quantification of mRNA levels can be also effected using an amplification reaction [e.g., PCR, "PCR Protocols: A Guide To Methods And Applications", Academic Press, San Diego, Calif. (1990)), employing primers, which hybridize specifically to the MRNA of a chemotactic receptor of interest.

A variety of controls may be usefully employed to improve accuracy in mRNA detection assays. For instance, samples may be hybridized to an irrelevant probe and treated with RNAse A prior to hybridization, to assess false hybridization.

Functional assays can also be used to determine the chemotactic receptor expression. For example, a chemotaxis assay which employs a gradient of the chemotactic agent (e.g., SDF-1) and follows stem cell migration through a membrane towards the chemotactic agent can be utilized to identify and isolate stem cells exhibiting increased chemotaxis. If the cells do not express enough levels of the chemotactic receptor (e.g., CXCR4), then the majority of the cells will remain on the membrane. However, upon increased expression of the chemoattractant receptor of the present invention, cells will migrate through the membrane and settle on the bottom of the well of the chemotaxis plate (see Example 1 of the Examples section).

It will be appreciated that a functional homing assay can also be utilized by the method of the present invention. Such an assay is described in Kollet (2001) Blood 97:3283-3291.

Immunofluorescent staining can also be employed in a functional assay for determining cellular morphology following exposure to HGF. As illustrated in FIG. 1a of Example 1 which follows, co-staining with anti CXCR4 and anti-mobilized actin antibodies uncovered changes in stem cell morphology (i.e., cell spreading and lamellipodia formation) following treatment with HGF.

Stem cells exhibiting an increased sensitivity to the chemoattractant can be used in a wide range of clinical applications.

Thus, according to another aspect of the present invention there is provided a method of treating a disorder requiring cell or tissue replacement. The method is effected by providing to a subject in need thereof a therapeutically effective amount of stem cells pretreated with HGF or an active portion thereof selected capable of increasing a level of at least one chemoattractant receptor of the stem cells as described hereinabove, to thereby treat the disorder requiring the cell or tissue replacement in the subject.

Disorders requiring cell or tissue replacement include but are not limited to various immunodeficiencies such as in T and/or B lymphocytes, or immune disorders, such as rheumatoid arthritis. Such immunodeficiencies may be the result of viral infections, HTLVI, HTLVII, HTLVIII, severe exposure to radiation, cancer therapy or the result of other medical treatment; Hematological deficiencies including but not limited to leukemias, such as acute lymphoblastic leukemia (ALL), acute nonlymphoblastic leukemia (ANLL), acute myelocytic leukemia (AML) or chronic myelocytic leukemia (CML). Other such hematological deficiencies can be, but are not limited to, severe combined immunodeficiency (SCID) syndromes (such as, for example adenosine deaminase (ADA) deficiency and X-linked SCID (XSCID)), osteopetrosis, aplastic anemia, Gaucher's disease, thalassemia and other congenital or genetically-determined hematopoietic abnormalities; Other disorders requiring cell or tissue replacement include those associated with liver failure, pancretic failure, neurological disorders, those disorders requiring augmented bone formation such as osteoartbritis, osteoporosis, traumatic or pathological conditions involving any of the connective tissues, such as a bone defects, connective tissue defects, skeletal defects or cartilage defects.

Preferred individual subjects according to the present invention are mammals such as canines, felines, ovines, porcines, equines, bovines and preferably humans.

The stem cells according to this aspect of the present invention are preferably obtained from the subject to be treated. However stem cells may also be obtained from a syngeneic, allogeneic and less preferably from a xenogeneic donor.

It will be appreciated that when allogeneic or xenogeneic stem cells are used, the recipient subject and/or cells are preferably treated to prevent graft versus host and host versus graft rejections. Immunosuppression protocols are well known in the art and some are disclosed in U.S. Pat. No. 6,447,765.

It will be appreciated that the stem cells of the present invention can be genetically modified to express any therapeutic gene such as an antiviral agent against hepatitis further described in U.S. Pat. No. 5,928,638.

The stem cells are transplanted into the recipient subject. This is generally effected using methods well known in the art, and usually involves injecting or introducing the treated stem cells into the subject using clinical tools well known by those skilled in the art (U.S. Pat. Nos. 6,447,765, 6,383,481, 6,143,292, and 6,326,198).

For example, introduction of the stem cells of the present invention can be effected via intravascular administration, including intravenous or intraarterial administration, intraperitoneal administration, and the like. Cells can be injected into a mol Fenwall infusion bag using sterile syringes or other sterile transfer mechanisms. The cells can then be immediately infused via IV administration over a period of time, such as 15 minutes, into a free flow IV line into the patient. In some embodiments, additional reagents such as buffers or salts may be added as well. The composition for administration must be formulated, produced and stored according to standard methods complying with proper sterility and stability.

Stem cell dosages can be determined according to the prescribed use. In general, in the case of parenteral administration, it is customary to administer from about 0.01 to about 5 million cells per kilogram of recipient body weight. The number of cells used will depend on the weight and condition of the recipient, the number of or frequency of administrations, and other variables known to those of skill in the art.

After administering the cells into the subject, the effect of the treatment may be evaluated, if desired, as known in the art. The treatment may be repeated as needed or required.

The invention also provides a pharmaceutical composition comprising a therapeutically effective amount of an HGF, or an active portion thereof to be administrated alone or co-administrated with SCF. More specifically the invention provides pharmaceutical compositions for treating a disorder requiring cell or tissue replacement.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "mnobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Increased HGF Mediated Motility and CXCR4 Mediated Migration of Human CD34+ Progenitors to an Injured Liver It is well known that HGF is upregulated in the injured liver [Armbrust (2002) Liver 22:486-494) and that addition of human HGF increases the levels of human albumin producing cells in $CCl_4$ injured-livers in engrafted immune deficient murine chimeras [Wang (2003) Blood (epub ahead of print)].

Therefore, it was hypothesized that HGF may also participate in the regulation of human CD34+ cell migration and recruitment to the injured liver.

Human cells—CB and adult mobilized peripheral blood (MPB) were obtained following informed consent and in accordance with procedures approved by the human ethics committee of the Weizinann Institute. CD34+ cell enrichment was effected using magnetic bead separation as previously described [Kollet (2001) Blood 97:3283-3291]. CXCR4 expression was determined by flow cytometry using purified anti human CXCR4 (clone 12G5, R&D, Minneapolis, Minn.) and secondary F(ab')2 fragment of goat anti mouse IgG FITC (Jackson, West Grove, Pa.).

Liver injury—Mice were injected intra peritoneously (IP) with 10, 15 or 30 µl/mouse of CCl4 and liver samples were collected within a few hours, or 1-2 days following injection, as indicated.

Immunocytochemsity—CB CD34+ enriched cells were incubated for 40 hours in RPMI supplemented with 10% FCS in the absence of cytokines, or in the presence of SCF (50 ng/ml, R&D), HGF (100 ng/ml, PeproTech) or both cytolines. Cells were plated on fibronectin (10 µg/cm², Calbiochem, San Diego, Calif.) coated glass cover slips (2 hours, 37° C., 5% CO2), fixed for 25 minutes in 3% paraformaldehyde, permeabilized for 5 minutes in 0.5% TritonX100, both in PBS. Cells were indirectly immunolabeled with rabbit anti human CXCR4 polyclonal Ab (Chemicon, Temecula, Calif.), washed extensively with PBS and incubated with Phalloidin-TRITC (Sigma, Rehovot, Ill.) and goat anti rabbit Alexa 488 (Molecular Probes, Eugene, Oreg.). Following extensive washing with PBS, samples were mounted in Elvanol (Mowiol 4-88; Hoechst, Frankfurt, Germany); All procedures were carried out in a humidified atmosphere, at room temperature. Immunofluorescence was viewed and analyzed using a BioRad confocal microscope, at 100× magnification.

Chemotaxis—Migration of enriched CD34+ cells towards a gradient of SDF-1 was determined by transwell assay as described [Peled (1999) Science 283:845-848]. CD34+ cells were incubated for 40 hours in RPMI supplemented with 10% FCS in the absence of human cytokines, or with SCF (50 ng/ml, 614 McKinley Place NE Minneapolis, Minn.), HGF (100 ng/ml, PeproTech, Rocky Hill, N.J.) or both cytokines prior to migration towards 125 ng/ml of SDF-1.

Results

Enriched CB CD34+ cells were cultured for 40 hours in the absence of cytokines, or in the presence of stem cell factor, which is known to induce CXCR4 expression and SDF-1 dependent migration [Peled (1999) Science 283:845-848], HGF or a combination of both cytokines. Cells were then incubated with anti CXCR4 and/or anti-polymerized actin, washed extensively with PBS and incubated with Phalloidin-TRITC and goat anti rabbit Alexa 488. While CD34+ cells cultured in the absence of cytokines maintained a round shape, cells cultured with SCF were spread and polarized. Interestingly, HGF alone induced formation of actin-based protrusions from the cell surface and the combination of SCF and HGF promoted lamellipodia formation, a phenotype distinct from that observed with SCF or HGF alone (data not shown). Most importantly, these cytoskeletal rearrangements were associated with CXCR4 upregulation (FIG. 1a) and a functionally enhanced chemotactic response to SDF-1 (FIG. 1b). HGF did not induce chemotaxis of human progenitors alone (data not shown). However, HGF increased the motility of human progenitors and synergized with SCF to potentiate both CXCR4 expression and SDF-1-induced directional migration.

These unexpected findings suggest an important role for HGF in facilitating motility and directional migration of human CD34+ cells in response to injured liver stress signals.

Increased expression of HGF MRNA in the BM and liver of irradiated mice.

Example 2

Irradiation Upregulates of HGF in the Liver and in the Bone Marrow

It was explored whether irradiation, which is used prior to transplantation and is known to upregulate a variety of cytokines such as SDF-1, induces upregulation of HGF in the liver and in the bone marrow.

NOD/SCID mice were sublethally irradiated (375 cGy). Liver and BM sample collected 24 and 48 hours later, together with a sample from a non-irradiated mouse, were homogenized in Tryreagent (MRC). The MRNA was extracted and subjected to RT-PCR with specific primers. FIG. 2 shows that expression of HGF is increased 1 irradiation in both, the BM and in the liver.

Example 3

HGF Synergies with SCF to Increase the Repopulating Potential of CB CD34+ Cells

As demonstrated in example 1, HGF increases the motility of human progenitors and synergies with SCF to potentiate both, CXCR4 expression and SDF-1-induced directional migration.

Further experiments were carried out to explore whether HGF synergies with SCF to increase the repopulating potential of hematopoietic precursors. Thus, human CB CD34+ cells were cultured in the presence of SCF, HGF or the combination of both. NOD/SCID mice were irradiated (375 cGy) and transplanted with the cultured cells. One month later, BM of transplanted mice was examined for the level of human engrafting cells.

CB CD34+ cells were cultured in the presence of SCF (50 ng/ml), HGF (100 ng/ml) or both, in 10% FCS+RPMI, for 36 h. NOD/SCID mice (3 per group) were irradiated (375 cGy) and transplanted 24 h later with cultured cells derived from 2×105 cells/mouse. One month later, BM of transplanted mice was examined for the level of human engrafting cells, by using anti human CD45-FITC Ab and FACSCalibur.

TABLE 2

| Treatment | Human cell engraftment (%) | | |
| --- | --- | --- | --- |
| Control | 16.9 | 10.2 | 2.6 |
| SCF | 23.6 | 19.3 | 1.5 |
| HGF | 7.9 | 7.4 | 16.9 |
| SCF + HGF | 7.0 | 33.7 | 21.2 |

The results in Table 2 show that cells treated with HGF alone repopulate BM similarly to the control cells and at a significant lesser extent than cells pretreated with SCF. In contrast cells co-stimulated with SCF and HGF show increased repopulation capability in comparison to cell treated with HGF or SCF alone.

Example 4

HGF Increases the Potential of BM Cells to Migrate Towards SDF-1 and the Rate of Progenitor Cell Mobilization, Following CCl4 Injury As demonstrated in example 1, ex-vivo HGF administration to progenitor stem cells induces CXCR4 expression on the cell surface and enhance migration of the cells to SDF-1.

The following experiments were carried out to find the effect of in vivo administration of HGF in repopulation following organ injury.

Figure 3:
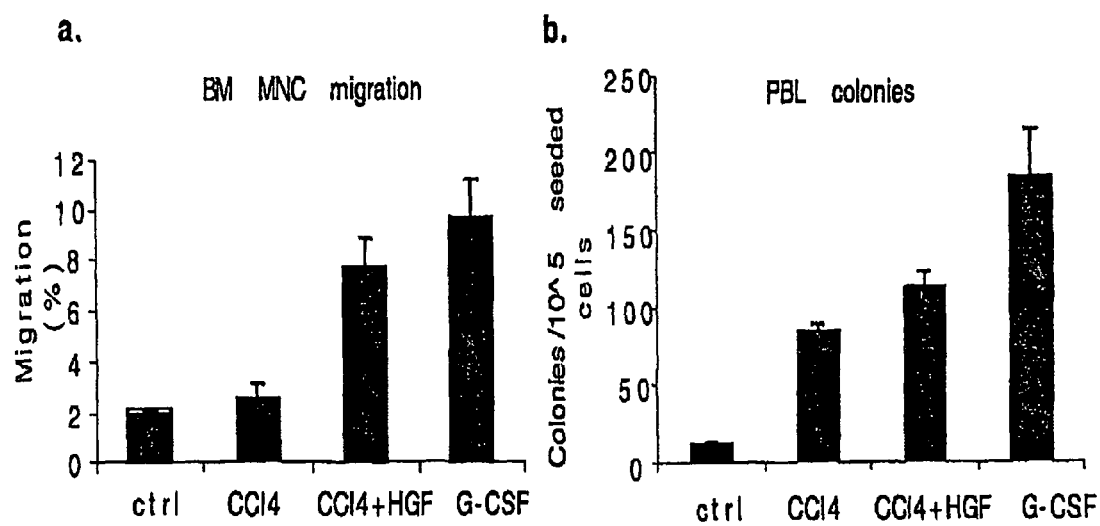
FIG. 3 Shows that HGF increases the potential of BM cells to migrate towards SDF-1 and the rate of progenitor cell mobilization, following CCl4 injury. NOD/SCID mice were treated with a single injection of CCl4 alone (10 ml, CCl4), or with CCl4 followed by 4 consecutive daily injections of HGF (1.5 mg/mouse, CCl4+HGF) starting 2 days later. SDF-1-induced migration by BM cells and the level of progenitors in the blood circulation of these mice were compared to non treated mice (ctrl) or to mice treated with G-SCF (300 mg/Kg, 5 consecutive days).

For that purpose, NOD/SCID mice were treated with CCl4 alone (to induce injury), with the combination of CCl4 followed by HGF or remained untreated (control). The mice were sacrificed, the bone marrow cells extracted, and migration of such BM cells to SDF-1 was monitored in-vitro (FIG. 3).

NOD/SCID mice were treated with a single injection of CCl4 alone (10 ml CCl4), or with CCl4 followed by 4 consecutive daily injections of HGF (1.5 mg/mouse, CCl4+HGF) starting 2 days later. SDF-1-induced migration by BM cells derived from these treated mice were compared to SDF-1-induced migration by BM cells derived from non treated mice (ctrl) or from mice treated with G-SCF (300 mg/Kg, 5 consecutive days).

BM cells isolated from CCl4 treated mice showed similar level of SDF-1 dependent migration as the level of migration obtained with BM cells from control non treated mice. In contrast, BM cells isolated from G-SCF treated mice showed enhanced level of SDF-1 dependent migration in comparison to the level of migration observed with BM from control non treated mice. Unexpectedly, BM cells isolated from mice receiving the combined treatment with HGF and CCl4 showed enhanced level of SDF-1 dependent migration in comparison to the level of migration observed with BM cells from CCl4 treated or non-treated mice.

In light of the increase in the migration capability of BM cells observed in HGF/CCl4 treated mice, it was hypothesized that HGF/CCl4 treated mice may exhibit also an increase in the level of precursor progenitor cell in the blood circulation, consequently to BM mobilization.

To explore this hypothesis, the number of progenitor precursors in the circulation was monitored in CCl4 treated, in CCl4 and HGF treated versus non-treated mice (FIG. 3).

The results obtained show that induction of injury or inflammation, by CCl4 treatment, increased the number of progenitor precursors in the blood circulation. This results suggests that induction of injury or inflammation by CCl4 facilitates mobilization of progenitor precursors from the bone marrow to the blood but at a lesser extent than the positive control for mobilization (see G-SCF). However, inflammation or injury induced by CCl4 treatment in combination with HGF administration, induced a further increase in the level of progenitor precursors in the blood circulation.

The results obtained suggest administration of HGF to a subject suffering of organ inflammation and/or injury, to facilitate self repopulation and/or self engraftment to the injured organ, due to increased progenitor levels in the cell blood circulation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of generating stem cells suitable for transplantation, the method comprising:
    (a) collecting stem cells expressing c-met;
    exposing said stem cells to hepatocyte growth factor (HGF) or an active portion thereof alone; and
    (c) isolating stem cells having CXCR4 levels above a predetermined threshold, to thereby generate stem cells suitable for transplantation.

2. The method of claim 1, wherein collecting said stem cells is effected by:
    (i) a stem cell mobilization procedure; and/or
    (ii) a surgical procedure.

3. The method of claim 1, wherein said stem cells are hematopoietic stem cells.

4. The method of claim 1, wherein said hematopoietic stem cells are $CD34^+$ hematopoietic stem cells.

5. The method of claim 4, wherein said hematopoietic stem cells are $CD34^+/CD38^{-/low}$ hematopoietic stem cells.

6. The method of claim 1, wherein said stem cells are mesenchymal stem cells.

7. The method of claim 1, wherein said exposing said stem cells to said HGF or said active portion thereof, is effected by:
    (i) expressing a polynucleotide encoding said HGF or an active portion thereof in said stem cells; and or
    (ii) contacting said stem cells with said HGF or an active portion thereof.

8. The method of claim 1, wherein said isolating stem cells having CXCR4 levels above said predetermined threshold is effected by FACS.

9. The method of claim 8, further comprising determining homing capabilities of said stem cells having CXCR4 levels above said predetermined threshold following step (c).

* * * * *